United States Patent [19]

Goldsmith et al.

[11] 4,362,994
[45] Dec. 7, 1982

[54] SELF ALARMING FIVE SINGLE ELECTRODES CONDUCTIVITY CELL

[75] Inventors: Herbert Goldsmith, Rockville; Richard M. Stilwell, Germantown, both of Md.

[73] Assignee: Chemed Corporation, Cincinnati, Ohio

[21] Appl. No.: 167,897

[22] Filed: Jul. 14, 1980

[51] Int. Cl.³ .......................................... G01N 27/42
[52] U.S. Cl. .................................. 324/449; 324/444; 324/446
[58] Field of Search .................... 324/444, 446, 449

[56] References Cited

U.S. PATENT DOCUMENTS 3,993,945  11/1976  Warmoth .......................... 324/449

FOREIGN PATENT DOCUMENTS 936045  9/1963  United Kingdom ................ 324/449

Primary Examiner—Michael J. Tokar
Attorney, Agent, or Firm—Browdy and Neimark

[57] ABSTRACT

A cell for measuring the conductivity of liquids flowing through the cell utilizing the Kelvin four-electrode system, plus a guard electrode, and a circuit to operate an alarm when the operating electrodes have reached a predetermined state of fouling. Thus, the invention cell self alarms when it has been fouled to the point where operating results will thereafter be impaired.

10 Claims, 3 Drawing Figures

SELF ALARMING FIVE SINGLE ELECTRODES CONDUCTIVITY CELL

This invention relates to cells for measuring the electrical conductivity of liquids. Conductivity is proportional to salinity, acidity, entrained solids, and other useful parameters of liquids. Applications for the invention include the monitoring of the conductivity of boiler water, monitoring of the conductivity of blood in various medical applications, and monitoring the conductivity of solutions used in the chemical and biochemical industries.

More particularly, the invention pertains to such cells comprising a body of electrical insulating material defining a bore through which the liquid flows. The electrodes of the invention are embedded into the dielectric material defining the bore, thus forming part of the surface of the bore to be contacted by the flowing liquid.

The invention comprises a set of four such annular electrodes, the outer ones of which are current or drive electrodes and are connected to a low impedance source of electrical power. The inner electrodes are connected to a high impedance amplifier and are thus the voltage electrodes. They respond to the input drive power with a voltage as driven by the current electrodes and as modified by the conductivity of the flowing liquid. This Kelvin type cell is well known in the prior art, see for example, U.S. Pat No. 3,993,945 to Warmoth.

The invention also includes a fifth electrode which is the so called guard electrode to ground leakage currents to thereby assure that the middle voltage electrodes respond only to the sensed drive current and the liquid's conductivity.

The invention is operated in a constant voltage mode. In operation, power is driven into the outer current electrode from a variable oscillator. This power splits into two parts; one part being a current flow through the liquid to the nearest fitting, thence through the metallic case and the remaining fitting and, finally, from the fitting through the liquid to the fifth grounded electrode; the second part being a current flowing through the liquid in the central bore, past the voltage electrodes and finally passing into the second current electrode where it is sensed by the current to voltage converter. The voltage measured across the inner voltage electrodes is dependent only upon the sensed current from this oscillator and the conductivity of the liquid in the cell. The voltage detected at the voltage electrodes is provided to a differential amplifier where it is compared with a reference signal. The output signal from this amplifier operates the oscillator, driving the current electrodes so as to maintain the voltage at the middle voltage electrodes at a predetermined constant voltage. As fouling occurs, the input power needed to maintain the voltage at the voltage electrodes constant increases. In all cases, the current sensed by the current to voltage converter is directly proportional to the conductivity of the liquid, and this current is used to drive a direct reading conductivity meter.

As fouling occurs at the current electrode surfaces within the cell contacting the liquid, which results in additional resistance thereat, the voltage at the voltage electrodes will remain unaffected since even if the voltage electrodes foul, the current passing through these electrodes is so low due to the high impedance of the differential amplifier to which they are connected, that any surface voltage drop will be insignificant. This assures that the current is correct for a particular value of conductivity even though the voltage across the current electrodes may increase due to this increased resistance arising from the fouling of the current electrodes.

By providing an alarm to be operated by this increased power supplied to the current electrodes at a predetermined level, which is provided by an additional adjustable set point voltage, the invention conductivity cell will alarm on its own when cleaning due to fouling is required.

This has been a substantial problem in the prior art because the fouled or unfouled condition of the electrodes is difficult to determine. In industrial applications, in order to assure proper operation, the cell was periodically cleaned on a regular basis regardless of its condition, because the fouled or unfouled condition of the electrodes is difficult to determine. This caused a substantial waste of manpower, wasted down time, and the like for the cleaning when the cleaning was not necessary. More importantly, cleaning might have been required earlier, and thus the cell produced erroneous results during the time the fouling had increased to an indesirable operation imparing level. In medical applications, human life is at stake and high reliability is a prime criterion. Thus, the alarming feature is even more important, indicating to the nurses and other users of the equipment that the instrument needs to be serviced. The invention is contemplated particularly for use with kidney dialysis machines.

In addition, the invention circuit will output a reading for conductivity and means are provided to temperature correct this reading so that it is accurate as an absolute value regardless of the temperature of the liquid being measured.

The invention also provides ground means at the liquid inlet and outlet fittings to ground any stray currents which might enter the system via that route. If these fittings are poorly grounded within the external electric power distribution system, any currents generated will be absorbed by the ground electrode as well as the current drive electrode whose low impedance and current sinking capability nullifies the effect of these currents upon the measuring system.

The above and other advantages of the invention will be pointed out or will become evident in the following detailed description and claims, and in the accompanying drawings also forming a part of the disclosure, in which:

Figure 1:
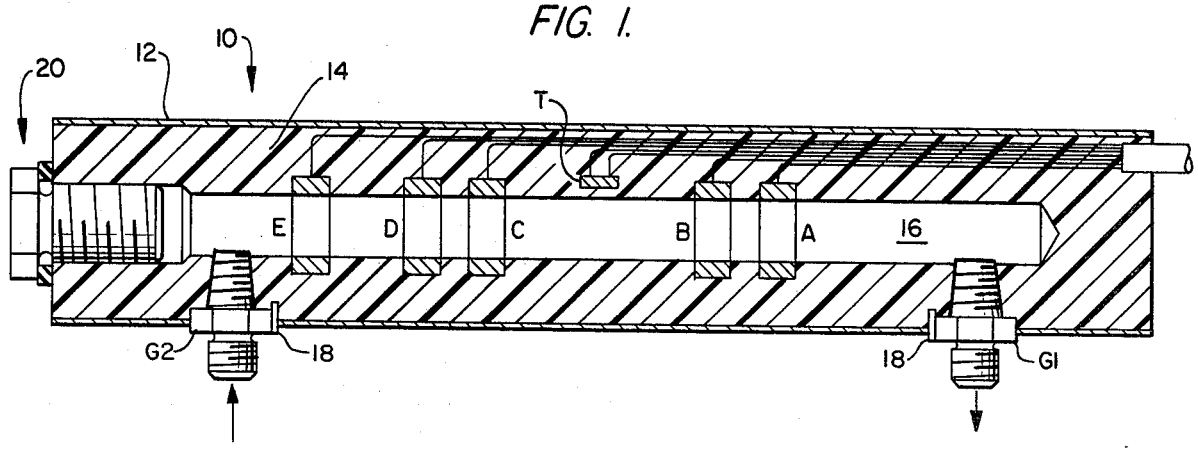
FIG. 1 is a cross-sectional elevational view of a cell embodying the invention.

Referring now in detail to the drawings, 10 indicates a conductivity cell embodying the invention. Cell 10 comprises an outer tube 12 which is filled with epoxy or the like dielectric material 14. A set of five generally annular electrodes A, B, C, D, and E are embedded in the dielectric material 14 as shown, and their wires are run through the material 14 as indicated. A thermistor T is located in close proximity to but not directly in contact with the fluid flow path 16 through the center of the cell 10 to sense temperature. A pair of side conduits extend out from the bore 16 and fittings G-1 and G-2 are provided to allow flow through the cell, as indicated by the arrows. Ground pins 18 are provided for cooperation with the metal tube 12 and fittings G-1 and G-2 to provide a better ground for stray currents that might enter through the pipes, conduits etc., with which cell 10 is used. The open of the bore 16 is closed off by an assemblage of a screw and a sealing washer 20, removal of which permits cleaning of the inside of the bore.

The outer shell of the cell is a metallic conductor which is connected electrically by ground pins to a pair of metallic fittings which provide for fluid flow into and out of the cell, as described below. The fittings are so located, in an alternate form, that their pipe threaded ends protrude slightly into the central bore through which fluid flows, so that the ends of these fittings will be cleaned when the electrodes are cleaned.

Figure 2:
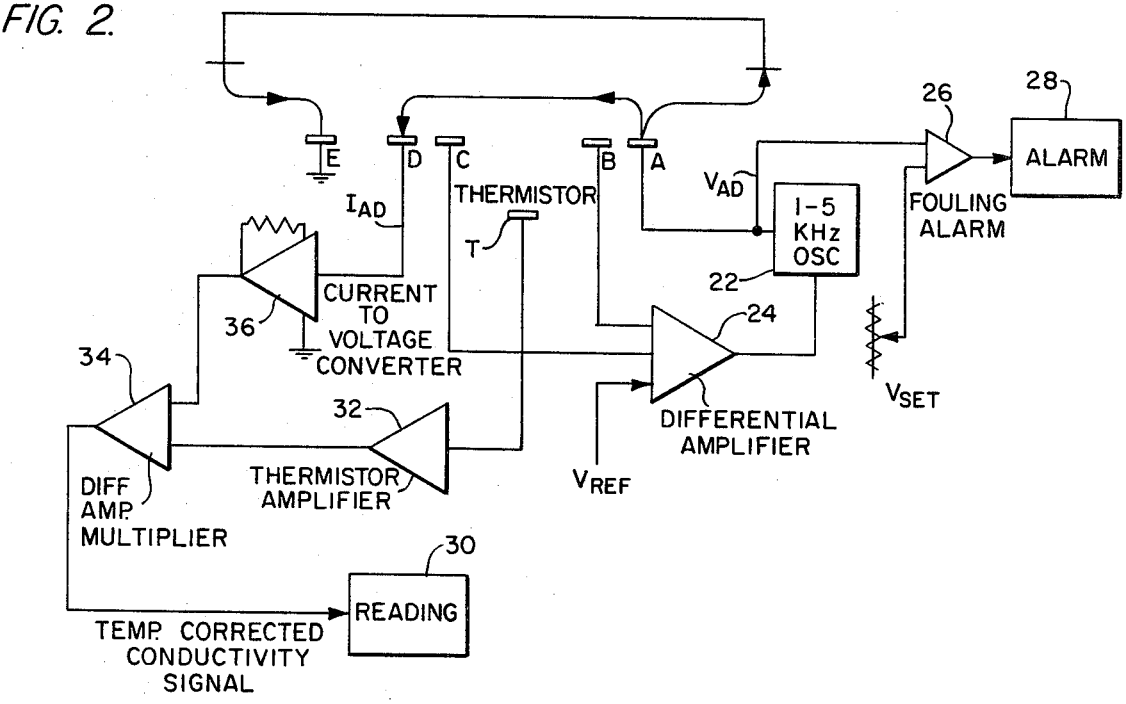
FIG. 2 is an electrical schematic diagram.

Referring now to FIG. 2, the outer electrodes A and D are the low impedance current or driving electrodes, and electrodes B and C are the driven or high impedance voltage electrodes, the voltage at which is kept constant to achieve the constant voltage mode of operation with its attendent advantages as set forth above.

This can be stated mathematically:

$$I_{AD} = V_{BC} G_{SOL} \cdot k \qquad \text{eq.(1)}$$

$$I_{AD} = (V_{AD}/R_{SY}) \qquad \text{eq.(2)}$$

$$V_{AD} = V_{BC} G_{SOL} R_{SY} \cdot k \qquad \text{eq.(3)}$$

where k is a constant dependent upon the geometry of the cell.

Equation 1 states that the resistance of the solution, the inverse of which is its conductivity G, times the voltage at BC, times the constant k, equals the current sensed at electrode D. This is in accordance with Ohm's Law, and is the basic premise of the Kelvin system wherein the outer are the current electrodes and the inner are the voltage electrodes, with the solution being the connecting medium.

In equation (2) the current sensed at the current electrode D is seen to be equal to the voltage at the AD electrodes divided by $R_{SY}$, the resistance of the current path through the central bore from electrodes A to D, and which is also responsive to the fouling of the electrodes A and D. That is, $R_{SY}$ increases as the electrodes foul.

By dividing eqs. (1) and (2) by each other and rearranging one comes to eq. (3) which says that if $V_{BC}$ is held constant, then the voltage at the current electrodes will respond to both the conductivity of the solution and the resistance of the system. If liquid conductivity holds steady, as in a steady state condition, then $V_{AD}$ will respond to the fouling of the electrodes. Similarly, with $V_{BC}$ held constant $V_{AD}$ will also respond to a change in conductivity, it being assumed that the fouling occurs slowly and not at one time. Thus, $B_{AD}$ responds to both $R_{SY}$ which is indicative of electrode fouling, as well as the solution conductivity. This is fortuitous, since a high value of $G_{SOL}$ indicates a large burden of dissolved solids, with a high probability for the formation of fowling precipitates, and this increases the sensitivity of $V_{AD}$ to any increase in the value of $R_{Sy}$ due to fouling.

Eq. (3) underlies the modus operandi of the invention. It shoudl be noted that $I_{Ad}$ drops out in the mathematics, and thus in the real cell that it is a nonimportant parameter as to the self alarming feature. However, $I_{AD}$ is proportional to conductivity generally, and is used to drive meter 30, as described in detail below.

Referring now to FIG. 2, electrode E is grounded. A low impendence oscillator 22 operating at a typical frequency of from 1-5 KHZ to eliminate polarization of the electrodes A and D drives the current electrode A under the control of and via the feedback from a high impedance differential amplifier 24. The voltage $V_{BC}$ picked up at the voltage electrodes is delivered to the amplifier 24 wherein it is compared to a reference voltage $B_{REF}$, and the output is used to drive the oscillator 22. The output of the oscillator 22, which is $V_{AD}$, is also provided to a comparator 26 which drives suitable alarm means 28. A predetermined set voltage $V_{SET}$ is also provided to the comparator 26, and when $V_{Ad}$ equals $V_{SET}$ then the comparator 26 will activate the alarm 28. The alarm 28 can take any form well known to those skilled in the various arts to which the invention pertains.

The circuit of FIG. 2 also provides means to drive an output reading device 30 which can comprise a meter graduated directly in units of conductivity or the like of the liquid. That is, the alarm means 28 which is an important advance of the invention is coupled with a conventional direct readout of conductivity or some other parameter in units of that parameter.

To this end, the signal from the thermistor is provided to an amplifier 32 and from there to a differential amplifier 34. The second input to amplifier 34 is $I_{AD}$ via a current to voltage converter 36. The conversion performed at the device 36 is necessary because of the particular circuit used, which is a voltage responsive circuit and the current $I_{AD}$ is the parameter which is proportional to the conductivity of the solution being measured, as indicated by equation (1) above, $V_{BC}$ being held constant as set forth above .

In this manner, the output of the differential amplifier 34 comprises a temperature corrected conductivity signal, in direct proportion to $I_{AD}$, which is used to drive the meter 30 in the usual manner.

Electrode E protects the normal operation of the Kelvin electrodes A, B, C and D by shunting all leakages from the case to ground.

Figure 3:
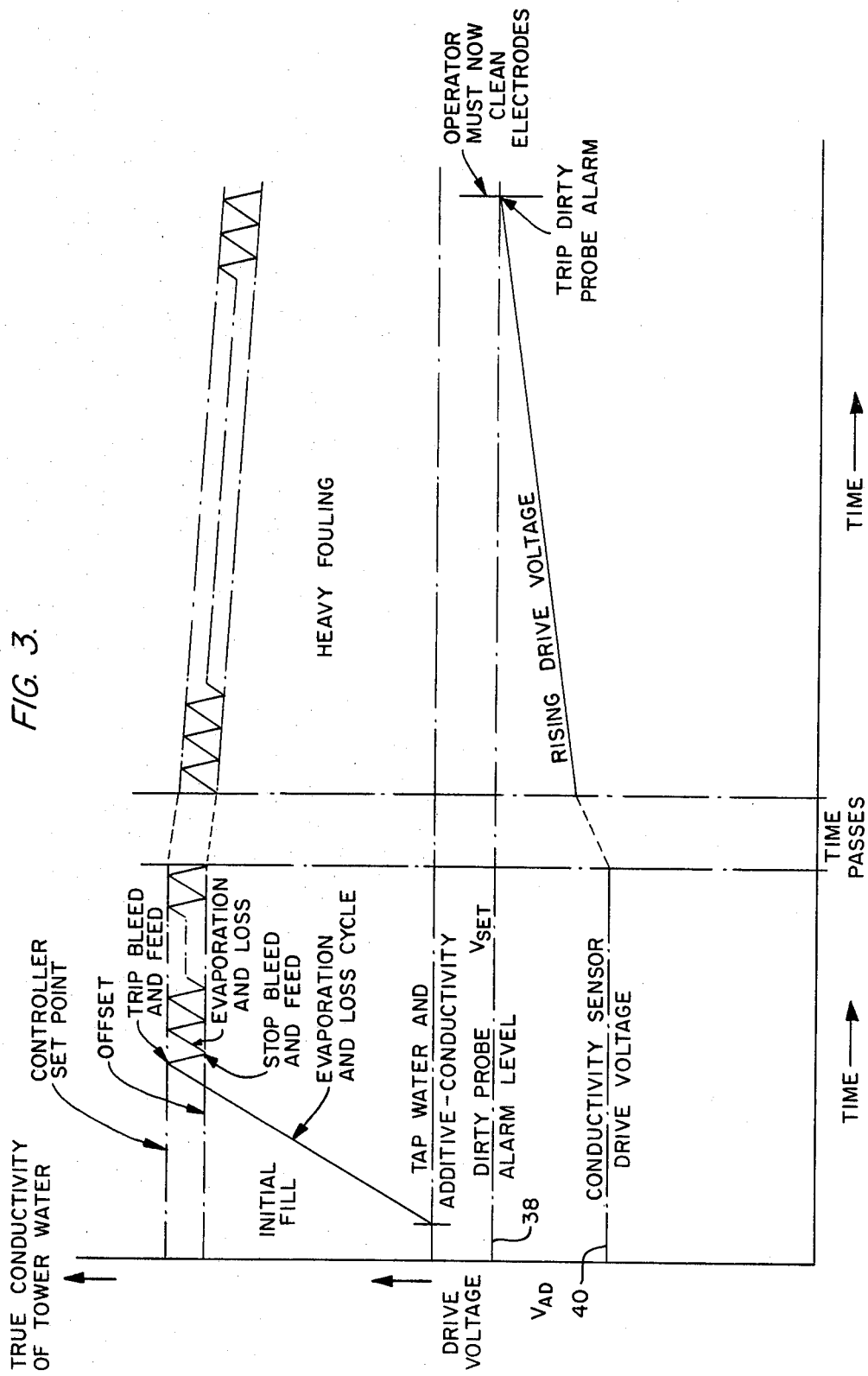
FIG. 3 is a chart to illustrate its operation.

Referring now to FIG. 3, line 38 corresponds to the set voltage $V_{SET}$ which is the predetermined value at which the alarm means 28 are to be activated in response to a predetermined amount of fouling at the electrodes A, and D. The line 40 corresponds to $V_{AD}$ which is the drive voltage producing $I_{AD}$ driving the conductivity cell circuit. As this voltage rises it will both operate the alarm when it reaches the line 38, and operate the meter 30 during normal operation prior that time.

The upper part of FIG. 3 indicates an application such as a typical tower controller which maintains the cooling-water conductivity within controlled limits. As the water evaporates the dissolved solids concentration and the conductivity increases. When this conductivity reaches a given set point, the cooling water is drained while at the same time tap water is admitted, thus lowering the conductivity to the desired value.

While the invention has been described in detail above, it is to be understood that this detailed description is by way of example only, and the protection granted is to be limited only within the spirit of the invention and the scope of the following claims.

We claim

1. A method of operating alarm means to indicate a predetermined condition of fouling of the electrodes in a conductivity cell, said cell being of a type comprising a pair of voltage electrodes arranged within a pair of current electrodes, all of said electrodes being arranged seriatim in the direction of fluid flow through the cell, comprising the steps of utilizing the power provided in said current electrodes which increases as said electrodes progressively foul during use of the cell to activate said alarm means when said power equals a predetermined value, and selecting said predetermined value to correspond to said predetermined condition of fouling.

2. The method of claim 1, arranging a ground electrode outboard of the current and voltage electrodes, in order to bypass spurious currents away from said current electrodes.

3. The method of claim 1, operating said voltage electrodes in a constant voltage mode, maintaining said voltage electrodes at a predetermined constant value, whereby the voltage of the power supplied to said voltage electrodes increases as said electrodes progressively foul, and using said supply voltage of said supply power to operate said alarm means when said supply voltage exceeds a predetermined value, said last mentioned predetermined value corresponding to said predetermined condition of fouling of said electrodes.

4. The method of claim 3, wherein said step of using said supply voltage is done by comparing said supply voltage to said predetermined voltage to operate said alarm means.

5. In a conductivity cell of a type comprising a pair of voltage electrodes arranged within a pair of current electrodes, a ground electrode arranged outboard of the current and voltage electrodes to bypass spurious currents to ground, and all of said electrodes being arranged seriatim in the direction of fluid flow through the cell, the improvement comprising alarm means, and an electrical circuit for utilizing the power provided to said current electrodes which increases as said electrodes progressively foul during use of the cell to operate said alarm means to indicate a predetermined condition of fouling of said electrodes.

6. The combination of claim 5, wherein said voltage electrodes are operated in a constant voltage mode with their voltage being held at a predetermined constant value, whereby the voltage of the power supplied to said current electrodes increases as said electrodes progressively foul, and using the supply voltage to operate said alarm means when said supply voltage exceeds a predetermined value, said last mentioned predetermined value corresponding to a predetermined condition of fouling of said electrodes.

7. The combinatin of claim 6, said means to use said supply voltage to operate said alarm means comprising a comparator, and means to supply said predetermined voltage and the supply voltage of said current electrodes to said comparator.

8. The combination of claim 5, said cell comprising a fluid flow passageway therethrough, a pair of fluid inlet and outlet grounded metallic fittings operatively cooperative with said passageway to flow fluid through said cell, the end of said fittings projecting slightly into said passageway, whereby said projecting ends of said fittings are cleaned when said passageway is cleaned.

9. The combination of cliam 5, an electrical circuit associated with said cell, one of said current electrodes being connected to a first electrical component in said circuit, said first component comprising ground means, and said one of said current electrodes being the electrode of said pair closest to said ground electrode.

10. The combination of claim 5, said cell comprising a fluid flow passageway therethrough, all of said voltage electrodes and said current electrodes being arranged in said cell so as to define portions of said fluid flow passageway, said cell comprising an opening at one end thereof, and removable sealing means to selectively close off said opening at said one end of said cell, whereby said cell passageway as well as the surface of said voltage and said current electrodes defining said passageway may be cleaned by removal of said sealing means to thereby permit access to said passageway.

* * * * *